(12) United States Patent
Coati et al.

(10) Patent No.: US 8,460,293 B2
(45) Date of Patent: Jun. 11, 2013

(54) INTRAMEDULLARY NAIL WITH SHAPE MEMORY ELEMENTS FOR ELONGATED BONES

(75) Inventors: Michele Coati, San Pietro in Cariano (IT); Mara Bagnasco, Milan (IT); Luigi Rossi, Peschiera del Grarda (IT); Graziano Marini, Caslot d'Azzano (IT); Graziano Rossi, Verona (IT)

(73) Assignee: Orthofix S.r.l. (IT)

( * ) Notice: Subject to any disclaimer, the term of this patent is extended or adjusted under 35 U.S.C. 154(b) by 232 days.

(21) Appl. No.: 13/030,896

(22) Filed: Feb. 18, 2011

(65) Prior Publication Data

US 2012/0172875 A1   Jul. 5, 2012

(30) Foreign Application Priority Data

Dec. 31, 2010 (EP) ..................................... 10197453

(51) Int. Cl.
*A61B 17/72* (2006.01)

(52) U.S. Cl.
USPC .......................................................... 606/62

(58) Field of Classification Search
USPC .............. 606/62–68, 304, 313, 323, 326, 327
See application file for complete search history.

(56) References Cited

U.S. PATENT DOCUMENTS

| | | |
|---|---|---|
| 5,415,660 A | 5/1995 | Campbell et al. |
| 5,702,215 A | 12/1997 | Li |
| 6,120,504 A | 9/2000 | Brumback et al. |
| 6,261,289 B1 | 7/2001 | Levy |
| 6,488,684 B2 | 12/2002 | Sterghos et al. |
| 6,575,973 B1 | 6/2003 | Shekalim |
| 7,828,802 B2 | 11/2010 | Levy et al. |
| 2004/0230193 A1 | 11/2004 | Cheung et al. |
| 2005/0159749 A1 | 7/2005 | Levy et al. |
| 2005/0187555 A1 | 8/2005 | Biedermann et al. |
| 2008/0262495 A1 | 10/2008 | Coati et al. |

FOREIGN PATENT DOCUMENTS

| | | |
|---|---|---|
| DE | 38 38 388 A1 | 5/1990 |
| DE | 20 2005 020 788 U1 | 7/2006 |
| EP | 0 772 420 A1 | 5/1997 |
| FR | 2 727 304 A | 5/1996 |
| FR | 2 783 702 A | 3/2000 |
| JP | 10-57398 A | 3/1998 |
| WO | 03/007830 A1 | 1/2003 |

*Primary Examiner* — Eduardo C Robert
*Assistant Examiner* — David Comstock
(74) *Attorney, Agent, or Firm* — Akerman Senterfitt

(57) ABSTRACT

An intramedullary nail for a fractured elongated bone, comprising a cannulated rod having proximal and distal ends; an outside tubular sleeve for coaxially hosting and guiding the rod; and at least a pair of shape memory elements hosted in corresponding seats at the distal end of the rod. Each shape memory element can be retractably housed in its seat in a first configuration, allowing insertion of the nail into the bone, and can project from a sleeve opening in another configuration. Pairs of transversal holes are provided in proximal portions of the rod and the sleeve. The distal pair of shape memory elements lie on an offset plane to the plane of the proximal holes and are kept in their corresponding seats by a distal cover fixed to the rod. This improves the stability of the nail in the medullary canal.

13 Claims, 7 Drawing Sheets

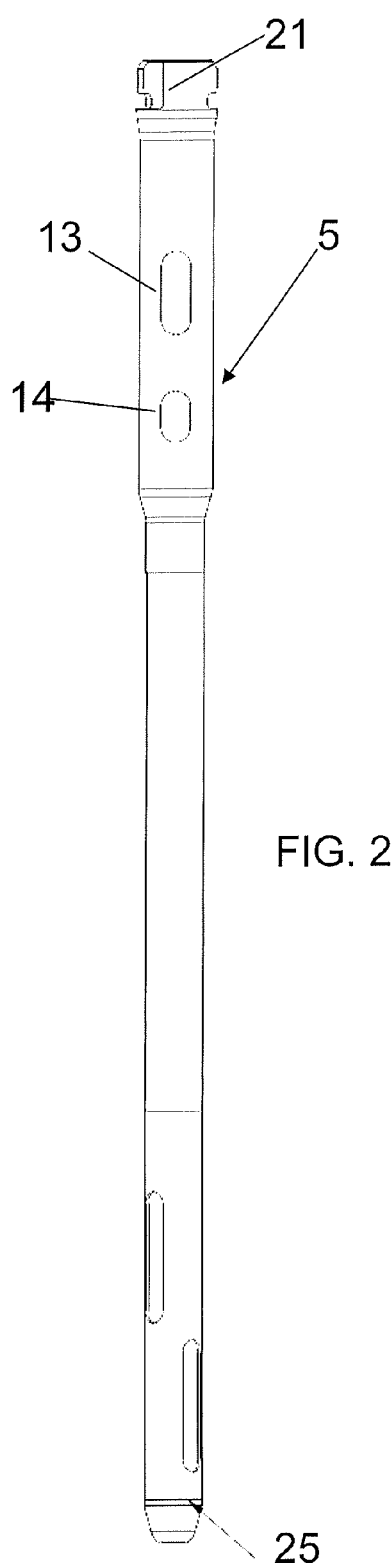
FIG. 2
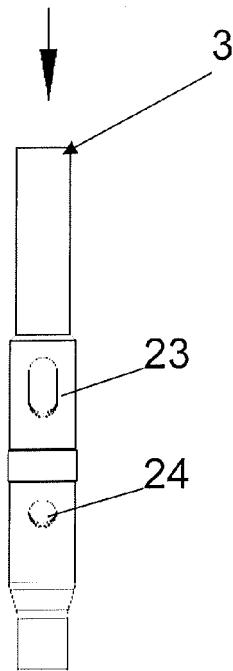
FIG. 3
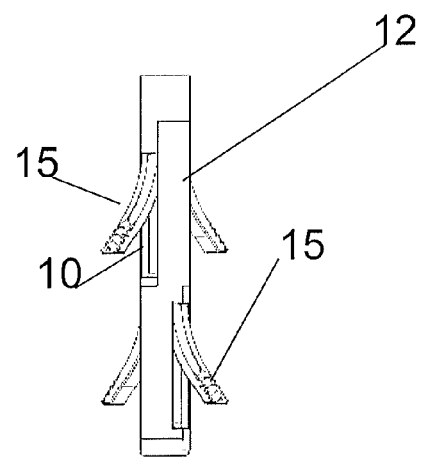

FIG. 4A
FIG. 4B
FIG. 4D
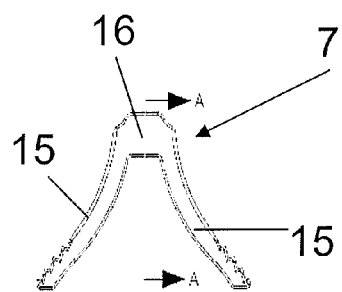
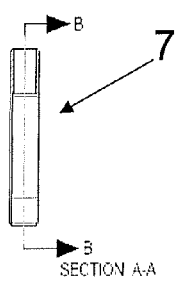
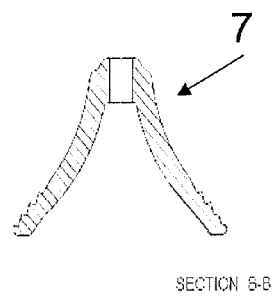
FIG. 4C

SCALE 2:1

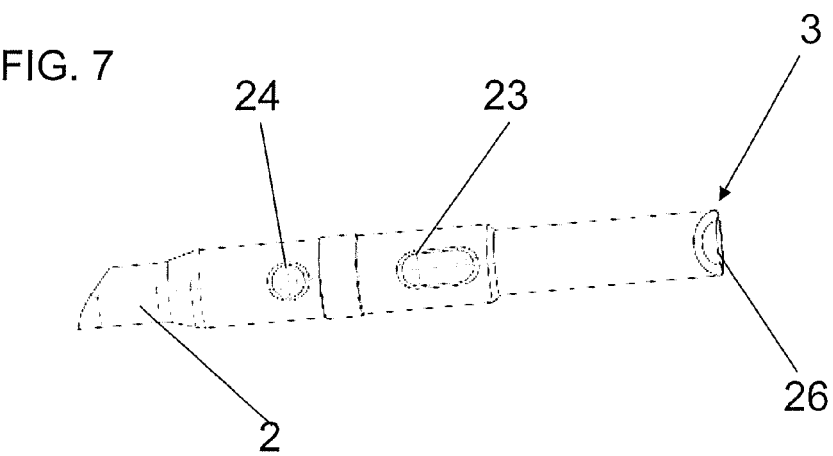
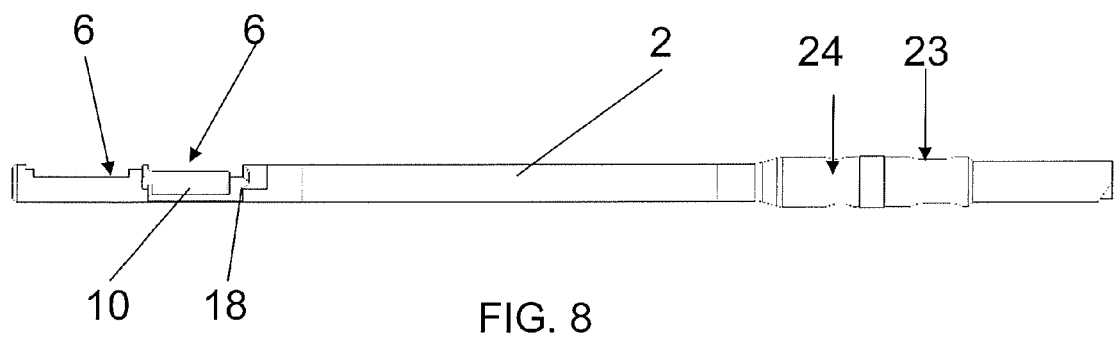

INTRAMEDULLARY NAIL WITH SHAPE MEMORY ELEMENTS FOR ELONGATED BONES

CROSS-REFERENCE TO RELATED APPLICATIONS

The present application claims priority to European Patent Application No. 10197453.3, filed Dec. 31, 2010, the entirety of which is incorporated herein by reference.

FIELD OF APPLICATION

The present invention refers, in its most general aspect, to an

Intramedullary nail suitable to be inserted into a fractured elongated bone, for example a femur or a tibia, and comprising a cannulated rod extending between a proximal end and a distal end.

More particularly, the invention relates to a nail comprising:
- a cannulated rod extending between a proximal end and a distal end;
- an outside tubular sleeve for hosting said rod, the rod being coaxial with the sleeve and axially guided inside the tubular sleeve;
- shape memory elements hosted in corresponding seats of said rod; each elements being able to assume a configuration wherein is retractably housed in its respective seats, so to allow the insertion of the nail in the bone, and another configuration wherein said elements are projecting from slots opening of said sleeve.

PRIOR ART

Intramedullary nails are known in the art to be used in surgical interventions and to be inserted into a fractured elongated bone to return consistency to the bone so that the bone callus regeneration mechanism can take place correctly Those nails comprise a stem or rod having a cylindrical shape either solid or hollow, in this last case the rod is cannulated.

In order to fix the intramedullary nail to the bone portions to be reconstructed, two offset holes are usually provided on the nail, having axis lying on parallel planes and extending diametrically across the rod in correspondence with the nail distal end. Other two offset holes are generally provided in correspondence with the nail proximal end with axis lying on parallel planes.

All these holes are suitable for housing bone screws that inserted in the bone after a convenient bone drilling thus fixing the intramedullary nail inside the fractured bone.

Although still widely used those known nails have known drawbacks due to bone drillings performed for the bone screw insertion in correspondence with the holes of the inserted intramedullary nail. Since the distal nail holes are no visible, X rays technique is involved with cumulative exposure of the operating staff and being quite awkward during the surgical operation.

Alternative nail structures have been provided in more recent times. For instance the European patent No. EP 1 740 113 owned by the same Applicant discloses an Intramedullary nail suitable for insertion in a fractured elongate bone and comprising a straight stem extending between a proximal end and a distal end and further comprises a plurality of elements realised with at least a shape-memory material. A free end of said shape-memory elements being positioned outwards the stem for the nail fixation to the bone.

Whilst advantageous from many points of views, such nails with shape-memory elements have some drawbacks that are still to be overcome.

For instance, the total missing of bone screws does not ensure complete stabilisation of the nail inside the medullary canal and against a high axial stress determined by the weight of a patient's body. If such stress is applied the nail becomes unstable and might even compromise the process of osteosynthesis as well as causing anomalies in the healing process.

The technical problem of the present invention is that of providing a Intramedullary nail having such structural and functional features to overcome all the drawbacks of the prior art solutions by a simpler nail construction for hosting the shape memory elements.

Another object of the nail of the present invention is that of providing a nail that might improve the stabilization phase before a final stable configuration is reached during the nail installation.

A further object of the present invention is that of providing an Intramedullary nail that might be easier to remove when the bone fracture is totally consolidated.

SUMMARY OF THE INVENTION

The solution idea at the basis of the present invention is that of providing a nail including an internal rod and an external sleeve and comprising shape memory elements associated only to the distal portion of said rod; the rod having a very simple construction including seats for the memory elements just in the distal portion and keeping the shape elements in their seats by a corresponding cover that is fixed to the rod. This allows realizing nails having shape memory elements in the distal part only while the proximal portion is provided with a hole and a slot opening for bone screws.

Based upon this idea for a solution, the technical problem is solved according to the invention by an Intramedullary nail to be inserted into a fractured elongated bone and comprising:
- a cannulated rod extending between a proximal end and a distal end;
- an outside tubular sleeve for hosting said rod, the rod being coaxial with the sleeve and axially guided inside the tubular sleeve;
- shape memory elements hosted in corresponding seats of said rod; each elements being able to assume a configuration wherein is retractably housed in its respective seats, so to allow the insertion of the nail in the bone, and another configuration wherein said elements are projecting from slots opening of said sleeve;

characterized in that:
- a distal couple of said elements is provided at the rod distal end;
- a couple of transversal holes being provided in the proximal portion of said rod and a couple of corresponding transversal holes being provided in the proximal portion of said sleeve, said holes having respective axis laying on a same plane;
- the shape memory elements of the distal couple laying on an offset plane with respect to the laying plane of the proximal hole and slot opening and being kept in their corresponding seats by a distal cover fixed to the rod.

Advantageously, the first and second shape memory element of the distal couple are 90° angularly spaced one from the other.

More particularly, a shape memory element of the distal couple is located on a plane at 45° with respect to the laying plane of proximal hole and slot opening while the other element of the distal couple is located on a plane at −45° with respect to the laying plane of the elements of the proximal couple.

It should be noted that the shape memory elements are realized by SIM (Stress Induced Martensite) materials, for instance an alloy of Nichel and Titanium.

Moreover, the distal cover is formed by two portions that are connected by one corner and are extended in perpendicular planes. Both said portions have an outside concave surface that reproduces the continuity of the cylindrical rod when the distal cover is mounted and fixed to the rod to keep in position the distal couple of shape memory elements.

The transversal holes of the proximal portion of the sleeve are slot openings while the transversal holes of the proximal portion of the rod are a passing hole and a slot openings.

Finally, a rounded tip is fixed to the distal end of said sleeve and this rounded tip has an open end.

Further features and advantages of the Intramedullary nail according to the invention shall become clearer from the following description of an example embodiment thereof, given for indicating and not limiting purposes with reference to the attached drawings.

BRIEF DESCRIPTION OF THE DRAWINGS

FIG. 2 illustrates an elevation view of a particular component of the nail of FIG. 1;

FIG. 3 illustrates an elevation view of another particular component of the nail of FIG. 1;

FIGS. 4A-4D illustrate front, side, top and cross section view of a shape memory element incorporated in the nail of the present invention;

FIG. 7 is a perspective view of a proximal portion of the particular component of FIG. 3;

FIG. 8 is a side elongated view of the particular component of FIG. 3;

DETAILED DESCRIPTION

Figure 1:
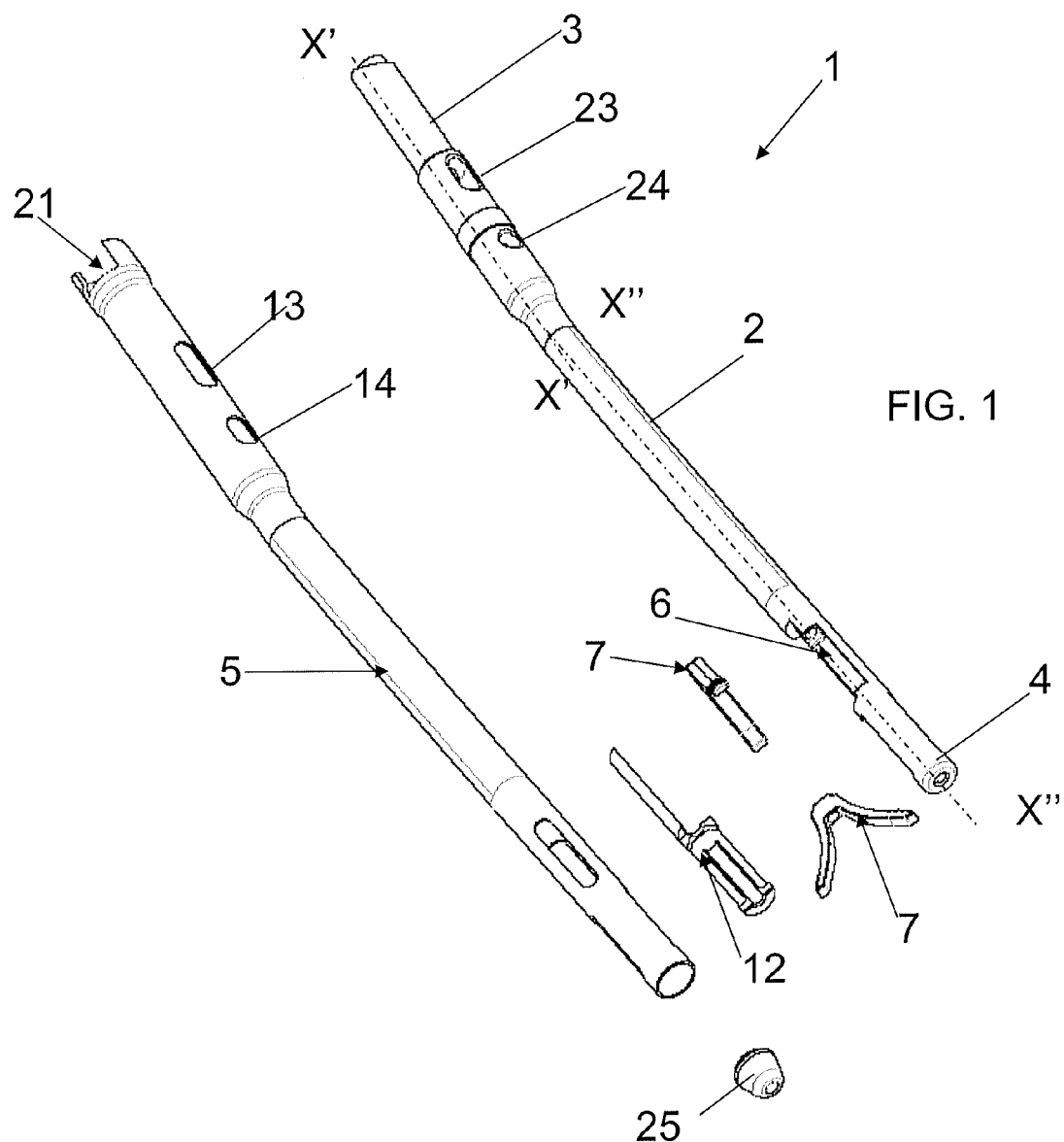
FIG. 1 illustrates a perspective view of a nail according to the invention split in its component portions.
Figure 5:
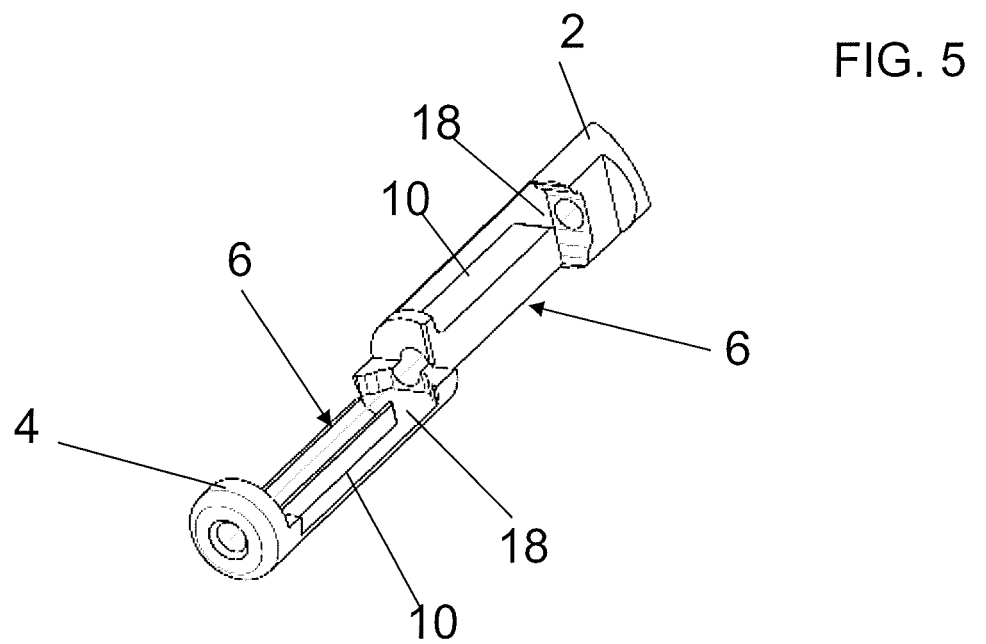
FIG. 5 illustrates a perspective view of a detail of the distal end of the particular of FIG. 3 with seats for the shape memory elements of FIG. 4.
Figure 6:
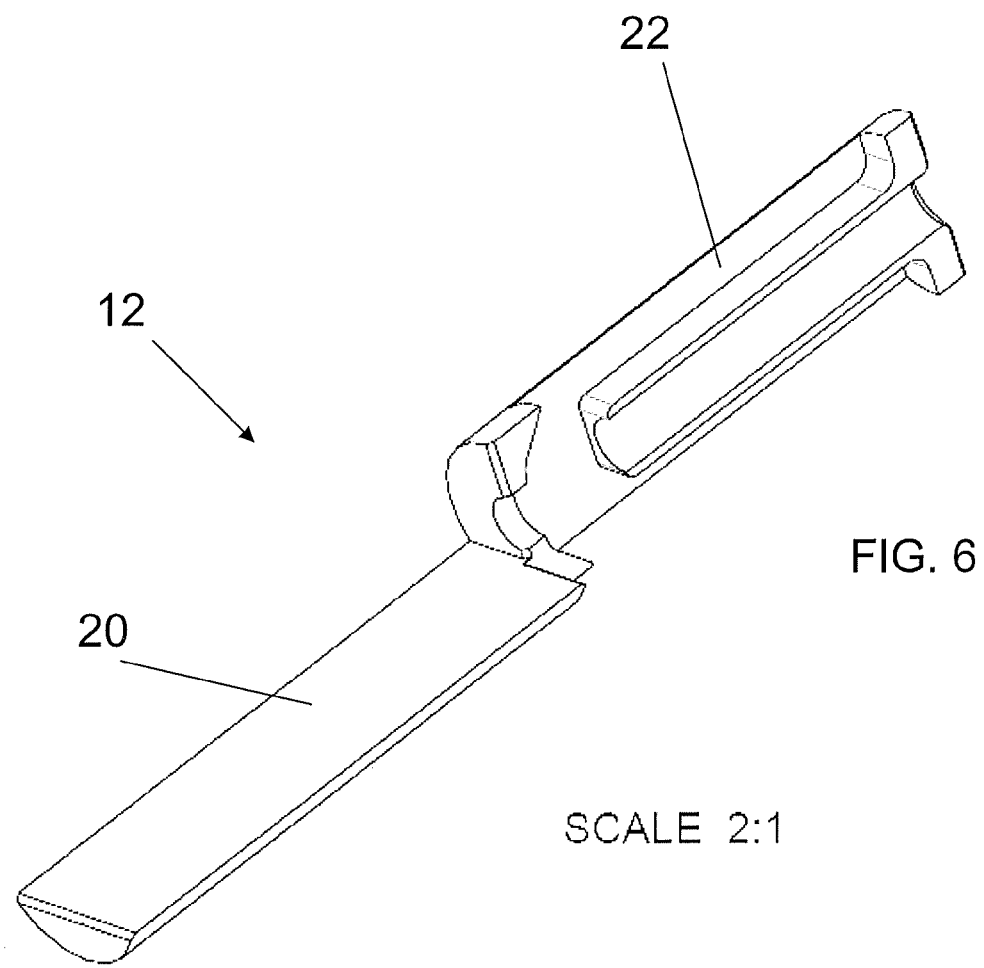
FIG. 6 is a perspective view of a further particular of the nail component shown in FIG. 3.
Figure 9:
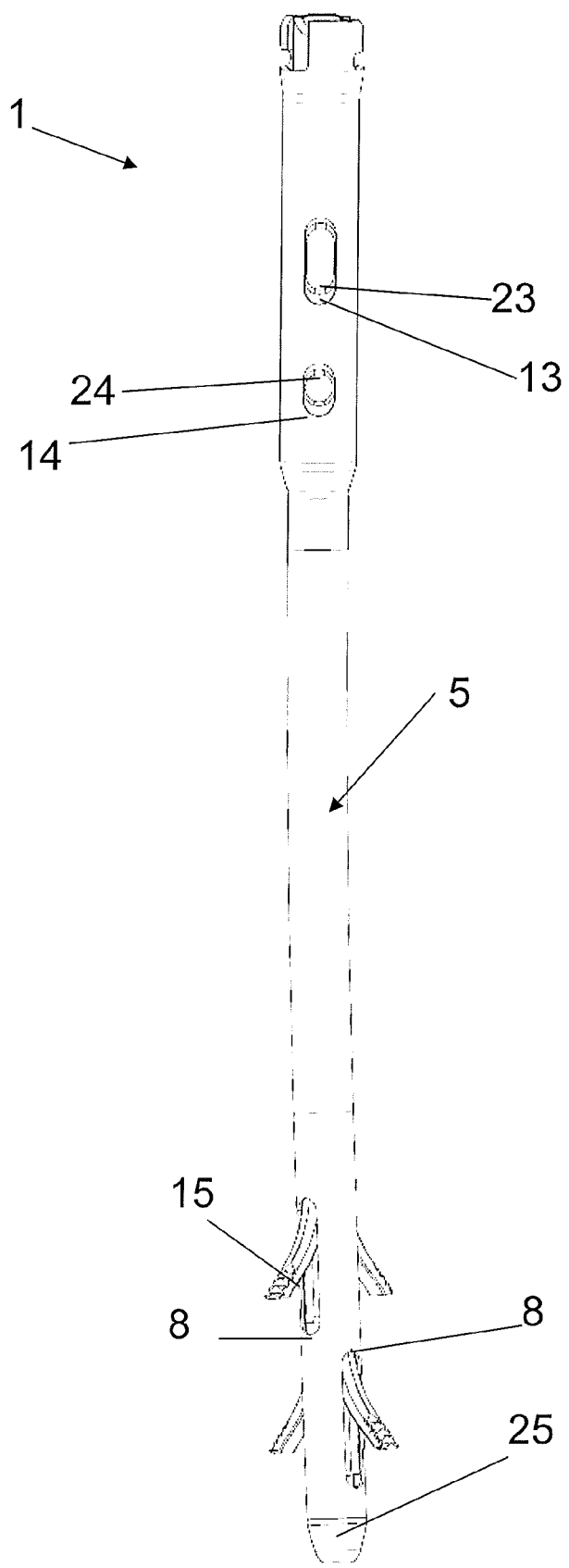
FIG. 9 is an elevated front view of the nail of the present invention in its assembled configuration.

With reference to the aforementioned figures, 1 generally indicates an intramedullary nail in accordance with the present invention, intended to be inserted into a fractured elongated bone, for instance a femur.

In case of femoral nail, the nail 1 is provided with an anatomic shape having proximal bent of 5° to follow the shape of the femoral bone.

The nail 1 comprises an inner rod 2 extending between a proximal end 3 and a distal end 4.

The nail 1 further comprises an outside tubular sleeve 5 hosting the rod 2 that is inserted coaxially into the tubular sleeve 5.

So, the nail 1 and its main components 2 and 5 are curved or bent so that the axis x'-x' of proximal end portion forms a small angle of 5° with the axis x"-x" of the remaining body and distal end portions of the nail 1.

Preferably, the nail 1 and its main components, the rod 2 and the sleeve 5 are cylindrical.

Both the sleeve 5 and the rod 2 comprise a couple of transversal holes in the proximal portion of both components; these holes have respective axis laying on a same plane.

More specifically, the sleeve 5 comprises a couple of proximal holes or slot openings 13 and 14 that are provided transversally with respect to the nail axis to allow the passage of bone screws.

The more proximal slot opening 13 is axially longer that the other slot opening 14.

Since the sleeve 5 is tubular, the openings 13, 14 are provided in opposite and coaxial portions of the perimeter wall of the sleeve proximal portion. Both slot openings 13, 14 have corresponding axis laying on a same laying plane.

So both proximal slot openings 13, 14 of the sleeve 5 are parallel one to the other.

Further slot openings 8 are provided in the distal portion of the sleeve 5. Those distal openings are angularly offset of 90° and angularly offset of +45° and −45° with respect to the laying plane of the axis of said proximal slot openings 13, 14.

The rod 2 shown in FIG. 2 is cannulated, that is to say that it has an internal cavity extending for at least a portion along a longitudinal axis, indicated with X. The rod may be totally cannulated for all its length and this feature is used to host a guide wire, for example a Kirschner wire, for use during the insertion into the bone medullary canal.

In accordance with the present invention the inner rod 2 is sliding hosted inside the tubular sleeve 5. More specifically, the rod 2 is axially movable inside the sleeve 5 and driven by an external device linked to the proximal end of the nail 1.

In this respect, even the rod 2 comprises a couple of proximal transversal passages 23, 24 in the proximal portion.

The more proximal passage 23 is a slot opening substantially corresponding in shape and extension with the slot opening 13 of the sleeve 5 when the rod 2 is in the right position inside the sleeve.

The other passage 24 is a passing hole for hosting a stabilization screw and this hole has its axis corresponding to the axis of the slot opening 14 when the rod 2 is in the right position inside the sleeve.

What is important is that the relative axially guided movement of the rod 2 inside the sleeve 5 could bring to a coincidence between slot openings 13, 14 in the sleeve 5 and the corresponding slot opening 23 and passing hole 24 in the rod 2.

In a head portion of the rod 2 a threading 26 is provided for a threaded connection with a suitable driving tool, not shown, for gripping the rod 2 of the nail 1.

In order to allow easy insertion of the nail 1 in the medullary canal it is foreseen an external instruments that may be connected to the proximal end 21 of the tubular sleeve 5. For allowing this connection the proximal end is shaped with an attachment system 22, for instance of the bayonet type; however, any other fastening system known in the field can be used.

The rod 2 comprises some distal seats 6 for hosting corresponding active elements 7 realised with at least a shape-memory material. The element 7 have the form of little wings 15 connected by a central portion or core 16.

The seats 6 are in the form of a passing opening 18 for hosting the core 16 of the active elements 7 and two lateral recesses 10 for hosting the wings 15 of the active elements when in the retracted position.

The active elements 7 are preferably similar to each other.

Because of their shape memory feature the elements 7 can assume different configurations from a first configuration wherein they are totally hidden inside their seat 6 to an extended configuration wherein they are protruding through corresponding slot openings 8 provided in the sleeve 5.

In other words, the active elements 7 are structured and suitable to take a first shape or configuration, wherein each elements 7 is retractably housed in its respective seats 6, with the wings 15 resting in the recesses 10, so to allow the insertion of the nail in the bone. Another shape or configuration is taken wherein said wings 15 of the active elements 7 are projecting from the respective recesses 10 of the seats 6 for abutting and gripping the internal wall of the medullary canal of the fractured bone.

With the term "shape memory material" we mean a material, known in the art, having a given starting shape and taking, under predetermined external conditions or undergoing a predetermined activation condition, called also "material instruction", a given new shape but returning to the initial shape conditions when the material instructions are deactivated.

For the meaning of the present invention, the starting shape may correspond to the configuration wherein the shape-memory elements 7 are arranged projecting from the seats 6 of the rod 2. However, according to the material used, the starting shape might even correspond to the configuration wherein the elements 7 are retracted.

It must be noted that, while the shape memory elements 7 may be realized with SME such as a Shape Memory Alloy, it is preferable to use SIM materials, that is to say: materials sensible to Stress Induced Martensite, for instance Nitinol that is an alloy of Nichel and Titanium.

Another characteristic of the shape-memory material stays in that the transition from the first to the second shape, or configuration, is reversible, i.e. the shape-memory elements can be transformed from the second to the first shape, or configuration, allowing the extraction of the nail from the bone.

The nail 1 of the invention is structured with a couple 11 of elements 7 located at the distal end 4 of the nail 1. We will call distal couple this couple 11 of shape memory elements 7.

Advantageously, the laying plane of one shape memory element 7 of the distal couple 11 is oriented at 45° with respect to the laying plane of the axis of the slot opening 24 and the passing hole 23 in the proximal portion of the rod 2.

The other element of the distal couple 11 is oriented at −45° with respect to said laying plane of the slot opening 24 and the passing hole 23.

Therefore, the first and second element 7 of the distal couple 11 are angularly spaced (or displaced) of 90° one from the other.

The fact that the distal elements 7 are offset with one another, for example with a offset of sexagesimal 90°, ensures a determined stability on orthogonal planes and it is useful for allowing a better gripping of the nail 1 inside the medullary canal.

Advantageously, the memory shape elements of the present invention are structurally independent from the rod 2 and are hosted in their corresponding seats 6 of the distal portion of rod 2 but firmly kept in such seats by a distal cover 12. The central core 16 of each elements 7 is firmly kept between the seat 6 and the cover 12, while the wings 15 of the elements 7 are movable through openings 10 left between the cover 12 and the rod 2 and through the slot openings 8.

The distal cover 12 has a shape that is conjugated with the shape and relative positions of the distal couple 11 of shape memory elements 7 to be covered.

The cover 12 is fixed to the corresponding distal rod portion by soldering or other fixing techniques.

The cover 12, once fixed to the rod, might be considered integral with the rod so that each seat 6 is formed by a passing opening 18 for hosting the core 16 of a shape memory element 7 and by a couple of opposite recesses 10 for hosting each wing 15 of the same shape memory element 7 when in the retracted configuration.

In more detail, the distal cover 12 is formed by two portions 20 and 22 that are connected at one corner and are extended in perpendicular planes.

Both portions 20, 22 have an outside concave surface that reproduces the continuity of the cylindrical rod 2 when the distal cover is mounted and fixed to the rod 2 to keep in position the distal couple 11 of shape memory elements 7.

The first portion 20 of the distal cover 12 is internally flat while the other portion 22 is shaped in order to abut against a corresponding and conjugated internal portion of the more distal seat 6.

The coupling between the distal cover 12 and the corresponding seats 6 always guarantee the continuity of the cannulated rod 2.

For facilitating the insertion of the nail 1 in the medully canal of the fractured bone, the tip portion of the sleeve 5 is preferably rounded so as to allow a sliding axial insertion of the nail in said medullary canal.

More specifically, a structurally independent rounded tip 25 is provided to be fixed to the distal end of the sleeve 5.

The tip 25 is soldered to the distal end of the sleeve 5 once the rod 2 has already been inserted into the sleeve.

It must be noted that such a tip 25 maintains the opening of the cannulated rod 2 having an open end.

As can be appreciated from what has been described, the intramedullary nail according to the present invention meets the requirements and overcomes the drawbacks mentioned in the introductory part of the present description with reference to the prior art solutions.

A clear advantage of the nail according to the present invention is due to the fact that just one transversal stabilizing screw provided in the proximal nail portion is needed to stabilize the nail in the medullary canal.

Another advantage of the combination of proximal screws with distal shape-memory elements is due to the fact that a nail so arranged has the double advantages of the shape-memory material nails and the classic nails with bone screws.

Of course, a person skilled in the art can apply numerous modifications and variants to the intramedullary nail described above, in order to satisfy contingent and specific requirements, all of which are covered by the scope of protection of the invention, as defined by the following claims.

The invention claimed is:

1. An intramedullary nail to be inserted into a fractured elongated bone and comprising:
    a cannulated rod extending between a proximal end and a distal end;
    an outside tubular sleeve for hosting said rod, the rod being coaxial with the sleeve and axially guided inside the tubular sleeve;
    shape memory elements hosted in corresponding seats of said rod; each element being able to assume a configuration in which it is retractably housed in its respective seat, so to allow the insertion of the nail in the bone, and another configuration in which said element projects from an opening slot of said sleeve;
    wherein:
    a distal pair of said elements is provided at the rod distal end;
    first and second pairs of transversal holes are provided in the proximal portion of said rod and first and second pairs of corresponding transversal holes are provided in the proximal portion of said sleeve, said pairs of holes having respective axes laying on a same plane, said first and second pairs of holes being suitable for housing a respective bone screw;

the shape memory elements of the distal pair lie on an offset plane with respect to the plane of said proximal holes and are kept in their corresponding seats by a distal cover, wherein said distal cover is mounted and fixed to the rod in such a manner to keep in position the distal pair of shape memory elements.

2. The intramedullary nail according to claim 1, wherein the first and second shape memory element of the distal pair are 90° angularly spaced one from the other.

3. The intramedullary nail according to claim 1, wherein one shape memory element of the distal pair is located on a plane at 45° with respect to the laying plane of said transversal holes while the other element of the distal pair is located on a plane at −45° with respect to the laying plane of said transversal holes.

4. The intramedullary nail according to claim 1, wherein said shape memory elements are realized by SIM (Stress Induced Martensite) materials.

5. The intramedullary nail according to claim 4, wherein said SIM material is an alloy of Nichel and Titanium, such as Nitinol.

6. The intramedullary nail according to claim 1, wherein the distal cover is formed by two portions that are connected by one corner and are extended in perpendicular planes.

7. The intramedullary nail according to claim 6, wherein both said portions have an outside concave surface that reproduces the continuity of the cylindrical rod when the distal cover is mounted and fixed to the rod to keep in position the distal couple of shape memory elements.

8. The intramedullary nail according to claim 1, wherein said transversal holes of the proximal portion of the sleeve are slot openings.

9. The intramedullary nail according to claim 1, wherein said transversal holes of the proximal portion of the rod are a passing hole and a slot openings.

10. The intramedullary nail according to claim 1, wherein a rounded tip is fixed to the distal end of said sleeve.

11. The intramedullary nail according to claim 10, wherein said rounded tip has an open end.

12. An intramedullary nail to be inserted into a fractured elongated bone and comprising:

a cannulated rod extending between a proximal end and a distal end;

an outside tubular sleeve for hosting said rod, the rod being coaxial with the sleeve and axially guided inside the tubular sleeve;

shape memory elements hosted in corresponding seats of said rod; each element being able to assume a configuration in which it is retractably housed in its respective seat, so to allow the insertion of the nail in the bone, and another configuration in which said element projects from an opening slot of said sleeve;

wherein:

a distal pair of said elements is provided at the rod distal end;

a pair of transversal holes are provided in the proximal portion of said rod and a pair of corresponding transversal holes are provided in the proximal portion of said sleeve, said holes having respective axes laying on a same plane;

the shape memory elements of the distal pair lie on an offset plane with respect to the plane of said proximal holes and are kept in their corresponding seats by a distal cover fixed to the rod; and the distal cover is formed by two portions that are connected by one corner and are extended in perpendicular planes.

13. The intramedullary nail according to claim 12, wherein both said portions have an outside concave surface that reproduces the continuity of the cylindrical rod when the distal cover is mounted and fixed to the rod to keep in position the distal couple of shape memory elements.

\* \* \* \* \*